United States Patent
Sartor et al.

(10) Patent No.: US 11,219,481 B2
(45) Date of Patent: Jan. 11, 2022

(54) SYSTEM CONFIGURED TO PROVIDE CONTROLLED DEPTH OF HEMOSTASIS

(71) Applicant: COVIDIEN LP, Mansfield, MA (US)

(72) Inventors: Joe D. Sartor, Longmont, CO (US); Arlen K. Ward, Englewood, CO (US)

(73) Assignee: Covidien LP, Mansfield, MA (US)

( * ) Notice: Subject to any disclaimer, the term of this patent is extended or adjusted under 35 U.S.C. 154(b) by 540 days.

(21) Appl. No.: 15/994,729

(22) Filed: May 31, 2018

(65) Prior Publication Data

US 2018/0271584 A1    Sep. 27, 2018

Related U.S. Application Data

(62) Division of application No. 14/159,900, filed on Jan. 21, 2014, now Pat. No. 9,993,287.
(Continued)

(51) Int. Cl.

| | |
|---|---|
| *A61B 18/12* | (2006.01) |
| *A61B 18/14* | (2006.01) |
| *A61B 18/18* | (2006.01) |
| *A61B 18/00* | (2006.01) |
| *A61B 90/00* | (2016.01) |

(52) U.S. Cl.
CPC ........ *A61B 18/1402* (2013.01); *A61B 18/148* (2013.01); *A61B 18/1233* (2013.01);
(Continued)

(58) Field of Classification Search
CPC . A61B 18/12; A61B 18/1206; A61B 18/1402; A61B 18/1442; A61B 18/1445; A61B 18/148; A61B 18/1233; A61B 2018/126; A61B 2018/1407; A61B 2018/1415; A61B 2018/143; A61B 2018/00595; A61B 2018/00607;
(Continued)

(56) References Cited

U.S. PATENT DOCUMENTS 4,228,800 A * 10/1980 Degler, Jr. ......... A61B 18/1402
                                                    606/48
4,263,900 A    4/1981 Nicholson
(Continued)

FOREIGN PATENT DOCUMENTS

| EP | 1510179 A1 | 3/2005 |
| EP | 2457532 A1 | 5/2012 |

(Continued)

OTHER PUBLICATIONS

Extended European Search Report from Application No. EP 14156966.5 dated Jul. 14, 2014.
(Continued)

*Primary Examiner* — Thomas A Giuliani
(74) *Attorney, Agent, or Firm* — Carter, DeLuca & Farrell LLP

(57) ABSTRACT

An electrosurgical device is provided and includes a handset having a shaft extending therefrom. The electrosurgical device includes a pair of electrodes disposed at a distal end of the shaft. One or more sensors are in operable communication with the pair of electrodes to detect a pressure applied thereto. The amount of electrosurgical energy that is transmitted to the pair of electrodes is proportional to the amount of pressure that is applied to the pair of electrodes and detected by the sensor.

12 Claims, 3 Drawing Sheets

Related U.S. Application Data

(60) Provisional application No. 61/780,389, filed on Mar. 13, 2013.

(52) U.S. Cl.
CPC .. *A61B 18/1815* (2013.01); *A61B 2018/00083* (2013.01); *A61B 2018/00595* (2013.01); *A61B 2018/00607* (2013.01); *A61B 2018/00642* (2013.01); *A61B 2018/00702* (2013.01); *A61B 2018/00708* (2013.01); *A61B 2018/00738* (2013.01); *A61B 2018/00875* (2013.01); *A61B 2018/1407* (2013.01); *A61B 2090/065* (2016.02)

(58) Field of Classification Search
CPC .......... A61B 2018/00642; A61B 2018/00648; A61B 2018/00666; A61B 2018/00702; A61B 2018/00708; A61B 2018/00738; A61B 2018/00875; A61B 2090/065
USPC .............. 606/32, 34, 38, 41, 42, 48, 50–52; 607/98, 99, 113, 115, 116, 145, 146
See application file for complete search history.

(56) References Cited

U.S. PATENT DOCUMENTS

| | | | |
|---|---|---|---|
| 5,954,717 A * | 9/1999 | Behl | A61B 18/1477 606/34 |
| 6,241,724 B1 * | 6/2001 | Fleischman | A61B 18/1492 600/374 |
| 6,464,697 B1 * | 10/2002 | Edwards | A61B 18/12 606/41 |
| 7,621,909 B2 | 11/2009 | Buchman, II et al. | |
| 8,343,150 B2 | 1/2013 | Artale | |
| 8,496,656 B2 | 7/2013 | Shields et al. | |
| 9,393,068 B1 * | 7/2016 | Leo | A61B 34/10 |
| 9,993,287 B2 | 6/2018 | Sartor et al. | |
| 2002/0123749 A1 * | 9/2002 | Jain | A61B 18/1492 606/41 |
| 2004/0199156 A1 | 10/2004 | Rioux et al. | |
| 2008/0020849 A1 | 1/2008 | Schlottmann | |
| 2008/0243118 A1 * | 10/2008 | Buchman | A61B 18/1402 606/41 |
| 2009/0270958 A1 | 10/2009 | Greenberg et al. | |
| 2011/0118736 A1 | 5/2011 | Harper et al. | |
| 2011/0306966 A1 | 12/2011 | Dietz | |
| 2012/0136348 A1 * | 5/2012 | Condie | A61B 18/1492 606/34 |

FOREIGN PATENT DOCUMENTS

| | | |
|---|---|---|
| EP | 2537480 A1 | 12/2012 |
| EP | 2090238 B1 | 4/2013 |
| WO | 2004010883 A1 | 2/2004 |

OTHER PUBLICATIONS

European Examinaiton Report issued in Application No. EP 14156966.5 dated Jan. 16, 2018 (6 pages).

* cited by examiner

SYSTEM CONFIGURED TO PROVIDE CONTROLLED DEPTH OF HEMOSTASIS

CROSS REFERENCE TO RELATED APPLICATION

The present application is a divisional application of U.S. patent application Ser. No. 14/159,900, filed on Jan. 21, 2014, now U.S. Pat. No. 9,993,287, which claims the benefit of and priority to U.S. Provisional Application Ser. No. 61/780,389, filed on Mar. 13, 2013. The entire contents of all of the foregoing applications are incorporated by reference herein.

BACKGROUND

Technical Field

The present disclosure relates to a system configured to provide controlled depth of hemostasis. More particularly, the present disclosure relates to a system including a pair of electrodes, an electrosurgical generator and controller that enables a user to intuitively control depth of hemostasis.

Description of Related Art

Electrosurgical devices (e.g., surface tissue desiccation devices) are well known in the medical arts and typically include a handset with an on/off switch, a shaft and at least one electrode operatively coupled to a distal end of the shaft that is configured to perform an electrosurgical procedure, such as surface tissue desiccation. The electrosurgical devices utilize electrical energy to effect hemostasis by heating the tissue and blood vessels.

Electrosurgical devices that utilize this electrical energy for treating various maladies of different organs like the liver, kidney, and spleen that include such things such as tumors, injuries from trauma, and such may have several shortcomings. These shortcomings may affect efficacy, morbidity and mortality. For example, a typical issue is the inability to adequately control blood loss during a tissue transection.

In an attempt to help overcome this particular limitation, various mono-polar and bi-polar RF electrosurgical devices have been created that act as conduits to deliver energy from an RF generator. These devices include electrocautery pencils and probes of various types and configurations from a number of different manufactures. The algorithms currently used with these electrosurgical devices in surgical treatments typically provide a constant amount of delivered energy in which the power level and duration are directly controlled by the user.

There may be particular drawbacks associated with delivering a constant amount of energy to target tissue, e.g., an inability to automatically adjust to the correct level of energy delivery by properly responding to the condition of the tissue being transected. After the initial application of energy to the target tissue the properties of the tissue begin to change. With these changes the application of energy should also change in order to maintain an optimum energy application. Typical methods of delivering hemostatic energy to the target tissue are ill-suited because these methods tend to rely on the user to adjust the energy delivery with little or no information or guidance as to the changing state of the target tissue. As a result the ultimate amount or duration of delivered energy may be insufficient for creating proper hemostasis.

Further, the typical energy delivery systems rely on the user to set the initial level of energy delivery with little or no relevant information of the condition of the target tissue being treated. Therefore, when using typical energy delivery systems, the initial application of energy can be significantly lower or higher than what is needed. When an inadequate amount of energy is applied to the target tissue, a hemostatic tissue effect may not be achieved. Likewise, if the duration of the energy application is too short, proper hemostasis will not be achieved or the tissue may carbonize. Carbonization prevents the continued flow of delivered energy to the tissue; it also often creates an overly superficial depth of treated tissue resulting in poor hemostasis.

SUMMARY

In view of the foregoing, a system including a pair of electrodes, an electrosurgical generator and controller that enable a user to intuitively control depth of hemostasis may prove useful in the medical field.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

As it is used herein, "electrosurgical procedure" generally refers to any electrosurgical procedure involving any form of energy, such as, for example, microwave energy and radiofrequency (RF) energy.

An aspect of the present disclosure provides an electrosurgical device. The electrosurgical device includes a handset having a shaft extending therefrom. The electrosurgical device includes a pair of electrodes disposed at a distal end of the shaft. One or more sensors. The sensor(s) is/are in operable communication with the pair of electrodes to detect a pressure applied thereto. The amount of electrosurgical energy that is transmitted to the pair of electrodes is proportional to the amount of pressure that is applied to the pair of electrodes and detected by the sensor.

The electrosurgical device may be configured to couple to an electrosurgical energy source configured to generate radio frequency energy that is transmitted to the pair of electrodes to electrosurgically treat tissue.

The sensor may be in operable communication with a controller of the electrosurgical energy source.

In certain instances, the pair of electrodes may be joined to form a closed loop configuration with an insulator therebetween. Alternately, the pair of electrodes may include a split configuration.

In certain instances, two or more sensors may be provided and may be in operative communication with a corresponding electrode of the pair of electrodes.

The pair of electrodes may be configured to operate in either a bipolar mode or monopolar mode of operation.

An aspect of the present disclosure provides an electrosurgical system. The electrosurgical system includes a source of electrosurgical energy including one or more processors and a controller for controlling an electrosurgical output of the source of electrosurgical energy. The electrosurgical system includes electrosurgical device including a handset having a shaft extending therefrom. The electrosurgical device includes a pair of electrodes disposed at a distal end of the shaft. One or more sensors is disposed at the distal end of the shaft and adjacent the pair of electrodes. The sensor(s) is in operable communication with the pair of electrodes to detect a pressure applied thereto. The amount of electrosurgical energy that is transmitted to the pair of electrodes is proportional to the amount of pressure that is applied to the pair of electrodes and detected by the sensor.

The sensor may be in operable communication with a controller of the electrosurgical energy source.

In certain instances, the pair of electrodes may be joined to form a closed loop configuration with an insulator therebetween. Alternately, the pair of electrodes may include a split configuration.

In certain instances, two or more sensors may be provided and may be in operative communication with a corresponding electrode of the pair of electrodes.

The pair of electrodes may be configured to operate in either a bipolar mode or monopolar mode of operation.

The pair of electrodes may be configured to operate in a bipolar mode and the pressure sensing is by correlation to electrode contact geometry by the impedance between the electrode pair as sensed in the controller of the electrosurgical generator.

An aspect of the present disclosure provides a method for electrosurgically treating tissue. An electrosurgical device including at least two electrodes and at least one sensor in operable communication with the at least two electrodes is provided. The sensor may be configured to detect pressure applied to the at least two electrodes. Pressure applied to the at least two electrodes is detected. And an electrosurgical output based on the detected pressure applied to the at least two electrodes is adjusted, wherein the electrosurgical output provided to the at least two electrodes is proportional to the pressure that is applied to the at least two electrodes.

A step of the method may include providing an electrosurgical energy source that is configured to generate radio frequency energy that is transmitted to the pair of electrodes to electrosurgically treat tissue.

The detected pressure from the sensor may be communicated to a controller of the electrosurgical energy source.

The pair of electrodes may be configured to include a closed loop configuration and an insulator therebetween. Alternately, the pair of electrodes may be configured to include a split configuration.

In certain instances, the electrosurgical device may be provided with two or more sensors that are in operative communication with a corresponding electrode of the pair of electrodes.

The electrosurgical device may be operated in a bipolar mode of operation.

BRIEF DESCRIPTION OF THE DRAWING

Various embodiments of the present disclosure are described hereinbelow with references to the drawings, wherein.

DETAILED DESCRIPTION

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
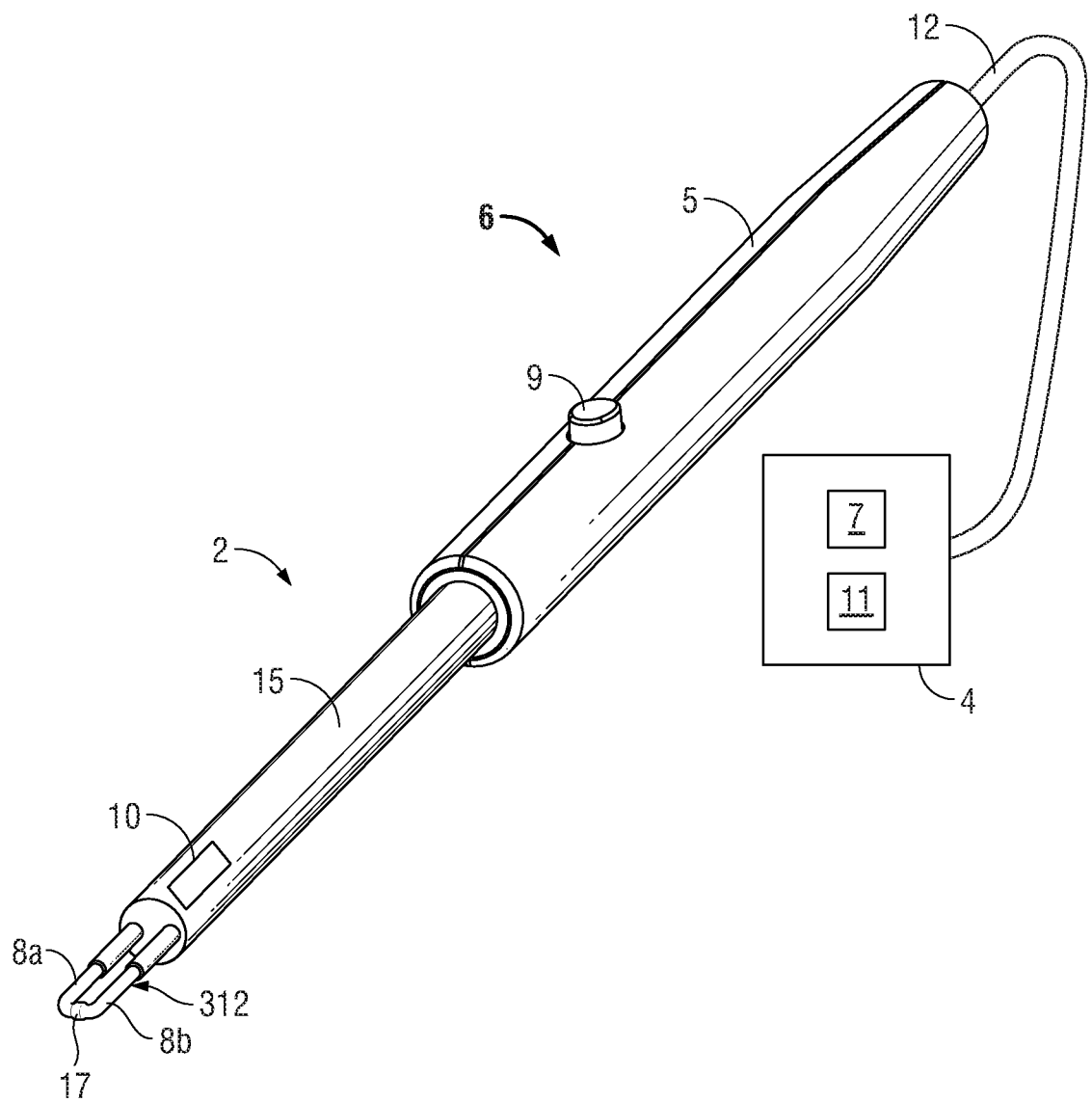
FIG. 1 is a perspective view of a system for electrosurgically treating tissue according to an embodiment of the present disclosure.

Referring to FIG. 1 there is shown a perspective view of an electrosurgical system 2 including a generator 4 having a controller 7, and an electrosurgical device 6 (device 6) for electrosurgically treating tissue according to an embodiment of the present disclosure. A cooling mechanism (not explicitly shown) may be provided for delivering fluid to electrodes 8a, 8b of electrosurgical device 6. In one embodiment the cooling system being composed of too cooling loops in electrical isolation from each other or in a second embodiment the cooling system circulated a fluid through the two electrodes where the fluid is non-conducting.

Continuing with reference to FIG. 1, generator 4 is configured to generate and deliver electrosurgical energy, e.g., radio frequency energy, to electrodes 8a, 8b for performing electrosurgical procedures. The electrosurgical procedures may include cutting, cauterizing coagulating, desiccating, and fulgurating tissue; all of which may employ RF energy. Generator 4 may be configured for monopolar and/or bipolar modes of operation. For illustrative purpose, generator 4 is shown configured for a bipolar mode of operation.

Generator 4 includes one or more processors 11 that are in operative communication with one or more control modules, e.g., controller 7, that are executable on processor 11. Controller 7 instructs one or more modules to transmit electrosurgical energy, which may be in the form of a wave or signal/pulse, via one or more cables 12 to device 6. Controller 7 and/or processor 11 includes one or more control algorithms that correlate tissue impedance at an electrode-tissue interface to a pressure applied to electrodes 8a, 8b, which is described in more detail below. One or more data lookup tables accessible by controller 7 and/or processor 11 may utilized to store relevant information pertaining to impedance and/or pressure. This information pertaining to impedance and/or pressure may be acquired empirically and/or calculated utilizing one or more suitable equations.

Device 6 can be any suitable type of electrosurgical device, including but not limited to electrocautery pencils and probes of various types that can grasp and/or perform any of the above mentioned electrosurgical procedures. For illustrative purposes, device 6 is shown as a bipolar electrocautery pencil (such as the one described in commonly-owned U.S. Pat. No. 7,621,909 to Buchman II, et al., the entire contents of which is hereby incorporated by reference) that includes a housing or handset 5. Handset 5 includes an on/off switch 9, a shaft 15 having two electrodes 8a, 8b at a distal end thereof and a sensor 10 that communicates with controller 7.

In embodiments, the bipolar electrocautery pencil may be configured for a monopolar mode of operation. In this instance, one of electrodes 8a or 8b of the bipolar electrocautery pencil serves as an active electrode and a return pad (not explicitly shown) may be positioned on a patient and utilized as a return electrode.

In embodiments where a cooling mechanism is provided for delivering fluid to electrodes 8a, 8b, one or more cooling tubes (not explicitly shown) may be provided on electrodes 8a, 8b. In this instance, the cooling tubes may be configured for open or closed loop configurations.

Electrodes 8a, 8b deliver electrosurgical energy, e.g., radio frequency energy, to tissue during operation of handset 5 for electrosurgically treating tissue, e.g., coagulating tissue. Electrodes 8a, 8b may include any suitable configuration. In accordance with the instant disclosure, electrodes 8a, 8b include a geometry that provides an increased electrode-tissue interface when electrodes 8a, 8b contact tissue and pressure is applied thereto. In the embodiment illustrated in FIG. 1, electrodes 8a, 8b are joined to form a closed loop configuration with an insulator 17 that separates electrodes 8a, 8b. For illustrative purposes, insulator 17 is shown as a "dimple" positioned between electrodes 8a, 8b.

Figure 4:
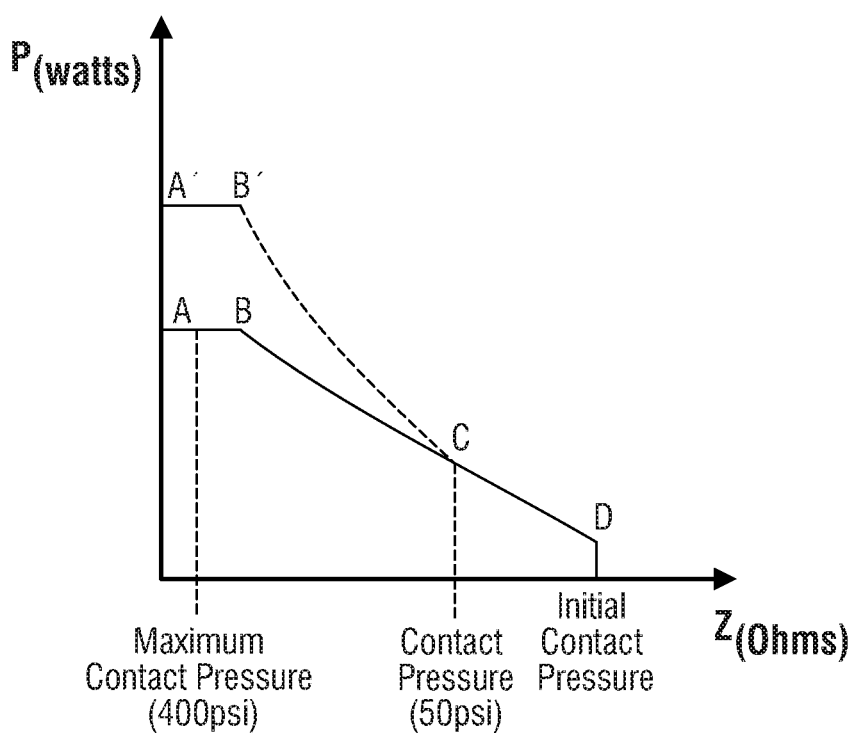
FIG. 4 is a graphical representation of power vs. impedance as it relates to pressure that is applied to electrodes of an electrosurgical instrument configured for use with the systems depicted in FIGS. 1 and 2.

FIG. 4 is a graphical representation of power vs. impedance as it relates to pressure that is applied to electrodes 8a, 8b of device 6. As illustrated in FIG. 4, as the force increases and contact area increases, impedance decreases such that in a region between a minimum force (e.g., 50 psi) and a maximum force (e.g., 400 psi) the power is increased at a rate greater than that of a constant voltage line.

In accordance with the instant disclosure, when electrodes 8a, 8b contact tissue with "soft" pressure being applied thereto, the electrode tissue interface is small, which correlates to a large impedance at the electrode-tissue interface, see point C in FIG. 4 for example. As used herein, "soft" pressure refers to applied pressure to tissue that may range from contact to about 50 psi. Likewise, when electrodes 8a, 8b contact tissue with "hard" pressure being applied thereto, the electrode tissue interface is large, which correlates to a small impedance at the electrode-tissue interface, see solid line between points A-B (or A'-B') in FIG. 4 for example. As used herein, "hard" pressure refers to applied pressure to tissue that may range from about 50 psi to about 400 psi; the upper range may correspond to the strength of tissue or the maximum force a surgeon can apply to the device 6. The pressure detected by sensor 10 is communicated to processor 11 of generator 4 and utilized to control an electrosurgical energy output of generator 4. The pressure differentiation between "soft" and "hard" pressure is also dependent on the physical geometry of the electrodes, with smaller diameters trending toward a higher pressure decision point. The example ranges above are based on a 0.125" diameter electrode with a hemispherical tip. One can appreciate that other pressures could be determined for use with tips having extended conical edges or shallow conical edges that blend from the hemispherical tip in a near stepwise profile.

In accordance with the instant disclosure, the pressure detected by sensor 10 is proportional to the electrosurgical energy output of generator 4. In particular, as the pressure applied to electrodes 8a, 8b increases (which correlates to impedance decreasing at the electrode-tissue interface) so too does the electrosurgical energy output to electrodes 8a, 8b (see solid line between points B-C in FIG. 4). Similarly, as the pressure applied to electrodes 8a, 8b decreases (which correlates to impedance increasing at the electrode-tissue interface) so too does the electrosurgical energy output to electrodes 8a, 8b (see solid line between points B-C in FIG. 4). Thus, if a user wants to apply more electrosurgical energy to tissue, such as, for example, if increased hemostasis to tissue is desired, e.g., to stop heavy bleeding during a resection procedure, the user would apply increased force or pressure on electrodes 8a, 8b against the tissue to increase the electrode-tissue interface.

In accordance with an embodiment of the present disclosure, controller 7 and/or processor 11 may utilize a non-linear control algorithm (see dashed lines between points B'-C in FIG. 4) with built-in safeguards to prevent short circuit at one boundary condition and arcing at another boundary condition. In particular, electrosurgical energy is capped at low ranges of impedance (see solid line between points A-B (or A'-B') in FIG. 4) and shut off completely at extremely low levels of impedance (see left of point A in FIG. 4) to prevent a short circuit from occurring. These low ranges of impedance correlate to relatively "hard" pressure being applied to electrodes 8a, 8b. Moreover, when the impedance rises above a certain level, power is limited to a fixed level (see point C and right thereof in FIG. 4) such that voltage at this point is maintained at a level that does not lead to arc initiation. These higher ranges of impedance correlate to relatively "soft" pressure (e.g., 50 psi) being applied to electrodes 8a, 8b, e.g., a gap may be present between electrodes 8a, 8b and tissue (see straight line between C-D). Impedances right of initial contact impedance (see point D) would deliver zero power.

Sensor 10 may be any suitable type of sensors known in the art including without limitation, pressure sensors, strain gauge sensors, impedance sensors, voltage sensors, current sensors, and the like. In the illustrated embodiment, sensor(s) 10 is a pressure sensor that is disposed at a distal end of device 6 adjacent electrodes 8a, 8b (FIG. 1). Sensor 10 is configured to detect a pressure applied to electrodes 8a, 8b and communicate this detected pressure to controller 7 of generator 4. The detected pressure correlates to an impedance of electrode-tissue interface. Sensor 10 communicates this pressure information to controller 7 and/or processor 11 for processing. Controller 7 then adjusts the electrosurgical energy output of generator 4 accordingly.

One or more resistors, transducer, accelerometers, etc. may be in operable communication with electrodes 8a, 8b and/or sensor 10 and may be configured to facilitate sensor 10 in obtaining information pertaining to pressure applied to electrodes 8a, 8b.

While system 2 has been described herein as being configured for use with a device 6, system 2 may be configured for use with other devices.

Figure 2:
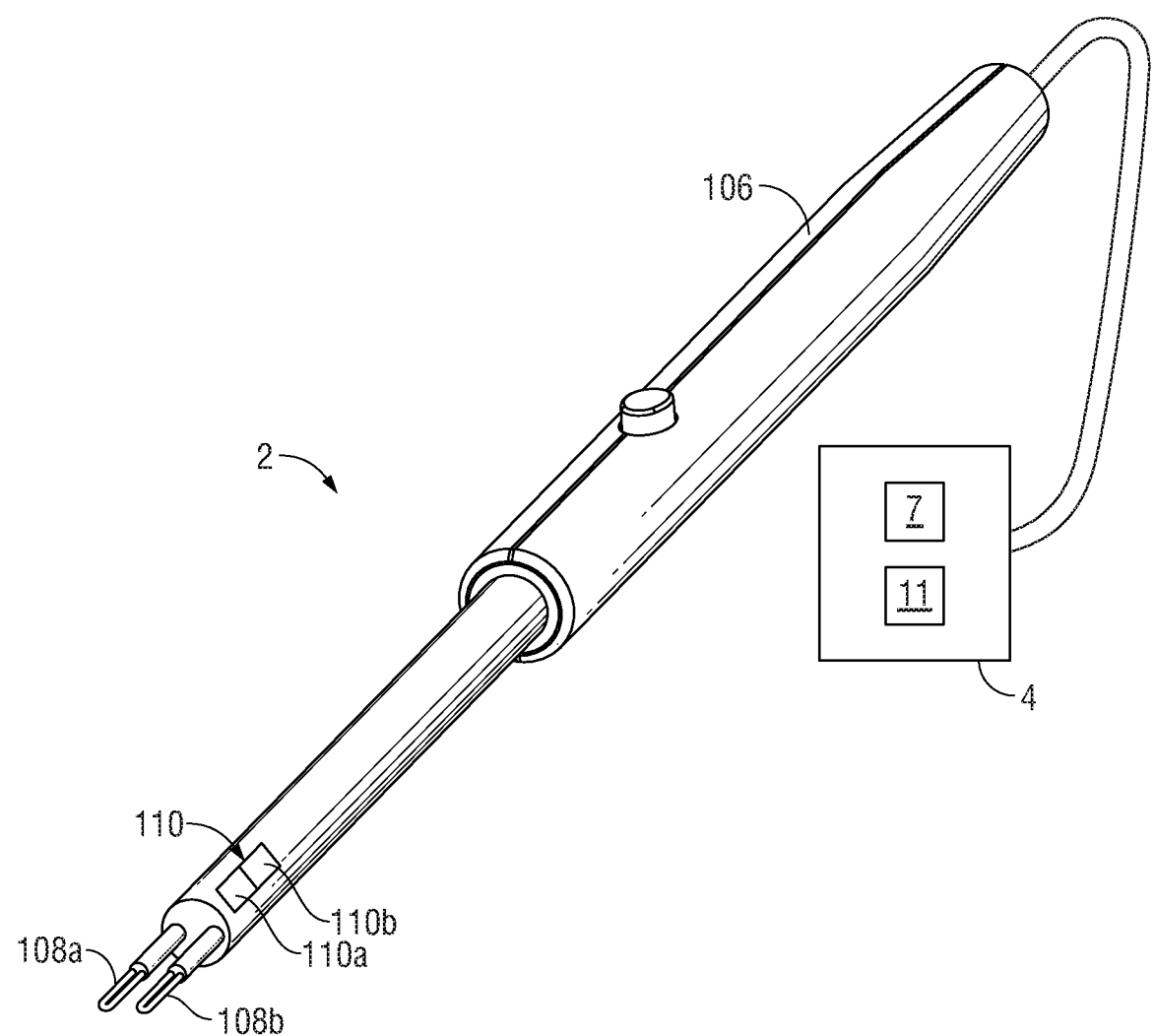
FIG. 2 is a perspective view of a system for electrosurgically treating tissue according to another embodiment of the present disclosure.
Figure 3:
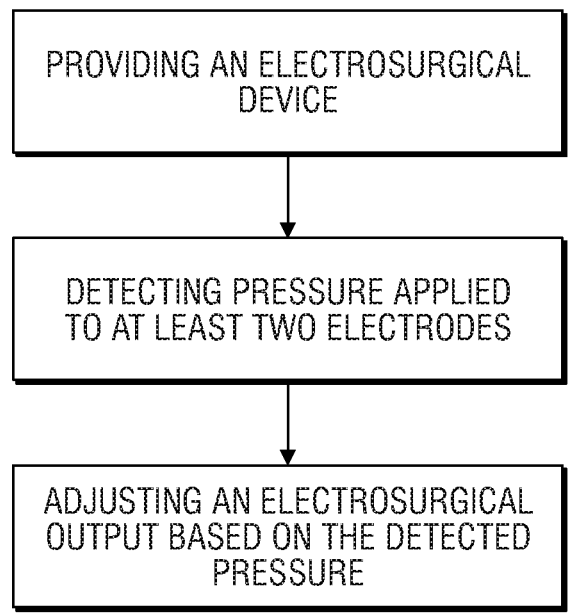
FIG. 3 is a flow chart illustrating a method of electrosurgically treating tissue.

For example, and with reference back to FIG. 2, there is shown a perspective view of a device 106 according to another embodiment of the present disclosure. Unlike device 6, device 106 includes an electrode configuration having electrodes 108a, 108b with a split configuration. In this instance, sensor(s) 110 is configured to individually communicate with each of electrodes 108a, 108b to detect pressure associated with each of electrodes 108a, 108b. In one particular embodiment, a pair of sensors 110a, 110b may be in operable communication with a corresponding electrode 108a, 108b. In this instance, each of sensors 10 may be configured to detect pressure at the corresponding electrodes Operation of the system 2 is described in terms of use with the device 6 for electrosurgically treating tissue, e.g., coagulating tissue.

In use, electrodes 8a, 8b are positioned to contact tissue. To increase electrosurgical energy that is transmitted to electrodes 8a, 8b, a surgeon applies a "hard" pressure to electrodes 8a, 8b to press electrodes 8a, 8b against tissue. The applied pressure is detected by sensor 10 and correlates to an electrode-tissue interface that is relatively large, which, in turn, correlates to small impedance at the electrode-tissue interface. That is, a large portion of a surface area of electrodes 8a, 8b contacts tissue. The detected pressure is communicated to processor 11 for processing. Processor 11 communicates a control signal to controller 7 to adjust the electrosurgical energy that is transmitted to electrodes 8a, 8b.

To decrease electrosurgical energy that is transmitted to electrodes 8a, 8b, a surgeon applies a "soft" pressure to electrodes 8a, 8b. This decrease of applied pressure is detected by sensor 10 and correlates to an electrode-tissue interface that is relatively small, which, in turn, correlates to large impedance at the electrode-tissue interface. That is, a small portion of a surface area of electrodes 8a, 8b contacts tissue. The detected pressure is communicated to processor 11 for processing. Processor 11 communicates a control signal to controller 7 to adjust the electrosurgical energy that is transmitted to electrodes 8a, 8b.

As can be appreciated, the aforementioned shortcomings described above with conventional electrosurgical devices are overcome by the unique configuration of sensor 10 and controller 11. That is, a surgeon can automatically control the electrosurgical output provided to electrodes 8a, 8b by pressing electrodes 8a, 8b against tissue with an appropriate amount of pressure. As can be appreciated, this may be particularly useful with surgical procedures that require immediate hemostasis of tissue, e.g., a liver resection.

From the foregoing and with reference to the various figure drawings, those skilled in the art will appreciate that certain modifications can also be made to the present disclosure without departing from the scope of the same. For example, electrodes 8a, 8b may be movable with respect to the shaft 15. In this instance, one or more types of resilient members may be coupled to electrodes 8a, 8b and configured to limit movement thereof when a pressure is applied thereto. In this instance, electrosurgical energy is transmitted to electrodes 8a, 8b when the electrodes 8a, 8b have moved a predetermined distance into shaft 15.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for electrosurgically treating tissue, comprising:
    providing an electrosurgical device including at least two electrodes and a sensor in operable communication with the at least two electrodes, the sensor configured to detect pressure applied to the at least two electrodes;
    detecting the pressure applied to the at least two electrodes;
    adjusting an electrosurgical output based on the detected pressure applied to the at least two electrodes setting initial power output at a constant non-zero voltage until a minimum contact pressure is reached; and
    increasing power in a non-linear manner to a second power output that is greater than initial power output after the minimum contact pressure is reached.

2. The method according to claim 1, including providing an electrosurgical energy source that is configured to generate radio frequency energy that is transmitted to the at least two electrodes to electrosurgically treat tissue.

3. The method according to claim 2, including communicating the detected pressure from the sensor to a controller of the electrosurgical energy source.

4. The method according to claim 1, including configuring the at least two electrodes to include a closed loop configuration and an insulator therebetween.

5. The method according to claim 1, including configuring the at least two electrodes to include a split configuration, providing the electrosurgical device with at least two sensors that are in operative communication with a corresponding electrode of the at least two electrodes and operating the electrosurgical device in a bipolar mode of operation.

6. The method according to claim 1, wherein the electrosurgical output provided to the at least two electrodes is based on the pressure that is applied to the at least two electrodes in a manner that yields increasing intensity of effect.

7. The method according to claim 1, wherein the sensor is configured to detect a change in an amount of pressure applied to tissue from a first non-zero pressure level to a second non-zero pressure level.

8. The method according to claim 7, wherein the electrosurgical output provided to the at least two electrodes is proportional to the detected change in the amount of pressure applied to the tissue and varied between a first non-zero amount corresponding to the first non-zero pressure level and a second non-zero amount corresponding to the second non-zero pressure level.

9. The method according to claim 1, further comprising operating the electrosurgical device in a bipolar mode of operation.

10. The method according to claim 1, further comprising measuring an impedance between the at least two electrodes.

11. The method according to claim 10, further comprising storing information pertaining to at least one of tissue impedance or pressure applied to the at least two electrodes.

12. The method according to claim 10, further comprising ceasing electrosurgical output if the measured impedance is below a threshold level.

* * * * *